(12) United States Patent
Brandt et al.

(10) Patent No.: US 7,214,514 B2
(45) Date of Patent: *May 8, 2007

(54) IDENTIFICATION OF HUMAN CELL LINES FOR THE PRODUCTION OF HUMAN PROTEINS BY ENDOGENOUS GENE ACTIVATION

(75) Inventors: Michael Brandt, Iffeldorf (DE); Reinhard Franze, Penzberg (DE); Ulrich Pessara, Weilheim (DE)

(73) Assignee: ROCHE Diagnostics, GmbH, Mannheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/982,880

(22) Filed: Nov. 8, 2004

(65) Prior Publication Data

US 2005/0090007 A1    Apr. 28, 2005

Related U.S. Application Data

(63) Continuation of application No. 10/112,755, filed on Apr. 2, 2002, now Pat. No. 6,846,673, which is a continuation of application No. 09/463,339, filed as application No. PCT/EP98/04584 on Jul. 22, 1998, now Pat. No. 6,395,484.

(30) Foreign Application Priority Data

Jul. 23, 1997  (EP) ................... 97112640
Dec. 1, 1997   (EP) ................... 97121073

(51) Int. Cl.
*C12P 21/02*        (2006.01)
(52) U.S. Cl. ..................... 435/69.6; 435/367
(58) Field of Classification Search ............... 435/350, 435/320.1, 69.1
See application file for complete search history.

(56) References Cited

U.S. PATENT DOCUMENTS

| | | | |
|---|---|---|---|
| 6,395,484 B1 * | 5/2002 | Brandt et al. ................ 435/6 |
| 6,548,296 B1 * | 4/2003 | Stern et al. ................ 435/366 |
| 6,555,373 B1 * | 4/2003 | Stern et al. ................ 435/366 |
| 6,846,673 B2 * | 1/2005 | Brandt et al. ............... 435/325 |

* cited by examiner

*Primary Examiner*—James Ketter
(74) *Attorney, Agent, or Firm*—Fulbright & Jaworski LLP (57) ABSTRACT

A process for selecting human cells for the production of human proteins by endogenous gene activation allows human proteins to be produced in economically feasible quantities and in a form suitable for producing a pharmaceutical composition. Also disclosed is a process for producing human proteins in a cell line identified in this matter.

13 Claims, 7 Drawing Sheets

Gene Activation Sequence

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 32 base pairs
      (B) TYPE: Nucleotide
      (C) STRANDEDNESS: single strand
      (D) TOPOLOGY: linear    (xi) SEQUENCE DESCRIPTION: SEQ ID NO: 1:

CGCGGCGGAT CCCAGGGAGC TGGGTTGACC GG       32

(2) INFORMATION FOR SEQ ID NO: 2:

(i) SEQUENCE CHARACTERISTICS:
      (A) LENGTH: 38 base pairs
      (B) TYPE: Nucleotide
      (C) STRANDEDNESS: single strand
      (D) TOPOLOGY: linear    (xi) SEQUENCE DESCRIPTION: SEQ ID NO: 2:

GGCCGCGAAT TCTCCGCGCC TGGCCGGGGT CCCTCAGC       38

(2) INFORMATION FOR SEQ ID NO: 3:

(i) SEQUENCE CHARACTERISTICS:
      (A) LENGTH: 36 base pairs
      (B) TYPE: Nucleotide
      (C) STRANDEDNESS: single strand
      (D) TOPOLOGY: linear    (xi) SEQUENCE DESCRIPTION: SEQ ID NO: 3:

CGCGGCGGAT CCTCTCCTCC CTCCCAAGCT GCAATC       36

(2) INFORMATION FOR SEQ ID NO: 4:

(i) SEQUENCE CHARACTERISTICS:
      (A) LENGTH: 36 base pairs
      (B) TYPE: Nucleotide
      (C) STRANDEDNESS: Single strand
      (D) TOPOLOGY: linear (xi) SEQUENCE DESCRIPTION: SEQ ID NO: 4:

GGCCGCGAAT TCTAGAACAG ATAGCCAGGC TGAGAG                    36

IDENTIFICATION OF HUMAN CELL LINES FOR THE PRODUCTION OF HUMAN PROTEINS BY ENDOGENOUS GENE ACTIVATION

This application is a continuation of application Ser. No. 10/112,755 filed Apr. 2, 2002 now U.S. Pat. No. 6,846,673, which is a continuation of application Ser. No. 09/463,339 filed May 30, 2000 now U.S. Pat. No. 6,395,484, which is a 371 of PCT/EP98/04584 filed Jul. 22, 1998, which claims priority of U.S. application Ser. No. 09/113,692 filed Jul. 10, 1998.

DESCRIPTION

The invention relates to a method for the selection of human cells for the preparation of human proteins by endogenous gene activation in order to produce human proteins in economical yields and in a form which is suitable for the production of a pharmaceutical preparation. The invention furthermore relates to a method for the production of human proteins in a cell line identified in this manner.

The production of human proteins by endogenous gene activation in a human cell line is known. For example, WO93/09222, WO94/12650, and WO95/31560 describe the production of human erythropoietin and other human proteins in human cell lines by endogenous gene activation.

In the documents cited, however, there is no mention of the fact that certain criteria must be observed in selecting the cell lines used for the production of human proteins. Therefore there can be no assurance that the desired human protein can be obtained in the desired yield and form, and free of contamination in the cell line chosen for its production. Accordingly, in the above-named documents only generally low yields of human proteins are achieved.

It was the objective of the present invention to eliminate the disadvantages of the state of the art and especially to offer criteria for the selection of human starting cell lines which are suitable for an endogenous activation of a predetermined target gene.

This objective is attained by a method for the selection of human cell lines for the production of human proteins by the activation of a target gene endogenously present in the cell line, characterized in that (a) a human cell line is tested for the presence of the following features:
  (i) a target gene with the desired nucleic acid sequence,
  (ii) at least 5 population doublings within 14 days in a suspension culture, and
  (iii) at least 5 population doublings within 14 days in a serum-free culture medium, and
(b) using a cell line having features (i), (ii), and (iii) as starting cell line for the endogenous activation of the target gene.

If one is facing the task of activating a human cell gene in a human cell line by gene targeting and obtaining a cell which is capable of the production of the target protein in satisfactory yield and in the desired form, according to the invention one will test several cell lines for the presence of a number of features which this cell line must possess in order to be a suitable candidate for the later large-scale production of the target protein. Preferably, immortalized cell lines, especially tumor cell lines, are tested since they have important advantages over non-immortalized cells regarding culturability.

According to feature (i) the human cell line is studied to see whether the target gene, i.e., the gene to be activated by endogenous gene activation, really has the desired nucleic acid sequence, generally the nucleic acid sequence of the natural target gene. Tumor cell lines and other cell lines in permanent culture often exhibit a series of mutations in their genome. Therefore it is an important aspect in the selection of a suitable cell line whether the cells have a correct gene for the desired product. The sequencing can be done by culturing the cells in the usual manner and sequencing the target gene. If necessary, the target gene can be amplified by PCR or other amplification methods prior to sequencing.

Another important feature for the selection of a cell line is culturability in suspension. Suspension cells are easier to ferment and the fermentation can be adapted more easily to larger dimensions, e.g., in a large fermenter with a capacity of, for example, 10 liters to 50,000 liters. Therefore the selected cells should be either suspension cells or they should easily adapt to a suspension culture. For this purpose the cells are cultured for 14 days with constant stirring. If the cells show at least five population doublings within this period they are considered suitable for suspension culture. Determining the number of population doublings can be done by periodically determining the cell count, e.g., by cell counting or by measuring the optical density of the cell suspension.

Another important feature in the selection of human cells is culturability in a serum-free medium. Since the purification of proteins from serum-free cell cultures is substantially easier and in serum-free culture there is no danger of contamination with animal pathogens, e.g., viruses, the selected cells should be able to grow in a serum-free culture. So the selected cells should be cultured for 14 days in a density of 1 to $10 \times 10^5$ cells per ml in culture vessels with a serum-free medium (e.g., RPMI 1640 with ITS by Boehringer Mannheim). If the cells during this culture show at least 5 doublings of population, which can be determined by cell counting, they are considered as suitable for serum-free culture.

Another important feature, and one preferred according to the invention is the generation time (iv). The selected cells in media such as, e.g., DMEM 10% fetal calf serum or RPMI 1640 with 10% fetal calf serum, have a high proliferation, i.e., they should have 10 to 256 population doublings, preferably 64 to 128 population doublings, within a week in culture. For this purpose the cells are seeded in culture dishes in a concentration of 0.1 to $10 \times 10^5$ cells per ml, preferably 0.5 to $2 \times 10^5$ cells per ml, and the cell count is made every two to three days by means of a cell chamber with or without trypsinization. Cells which show a sufficiently short generation time are especially suitable for large-scale production of human proteins by endogenous gene activation.

Another preferred feature is the absence of any detectable endogenous expression, i.e., transcription and translation, of the target gene (v). Preferably, for the endogenous gene activation, those cell lines are selected which have substantially no endogenous expression of the target gene. For this purpose the cells can be seeded in a cell density of 0.01 to $2 \times 10^6$ cells/ml, preferably 0.5 to $1 \times 10^6$ cells/ml of culture medium. After a predetermined time, e.g., 24 hours, the cell supernatant is removed, the cells are discarded, and the content of the target protein is determined in the cell supernatant by known test methods, e.g, ELISA. In the case of EPO the detection limit is, for example, 10 pg/EPO/ml. Cells seeded at $10^6$ cells/ml, which synthesize less than 10 pg of protein are considered as nonproductive and are especially suitable.

Still another important and preferred feature is the polysomia of the target gene in the cell to be selected (vi). The presence of more than two chromosomal copies of the target gene in the cell significantly increases the yields in the homologous recombination. For the production of EPO whose gene is on chromosome 7, the cells Namalwa (Nadkarni et al., Cancer 23 (1969), 64–79) or HeLa S3 (Puck et al., J. Exp. Med. 103 (1956),273–284), which have chromosome 7 in triplicate, have proven especially suitable. Additional examples of cell lines which contain chromosome 7 in a great number of copies are the colon adenocarcinoma cell line SW-480 (ATCC CCL-228; Leibovitz et al., Cancer Res. 36(1976), 4562–4567), the malignant melanoma cell line SK-MEL-3 (ATCC HTB 69; Fogh and Tremp in: Human Tumor Cells in vitro, pp. 115–159, J. Fogh (ed.), Plenum Press, New York 1975), the colon adenocarcinoma cell Colo-320 (ATCC CCL-220; Quinn et al., Cancer Res. 39 (1979), 4914–4924), the melanoma cell line MEL-HO (DSM ACC 62; Holzmann et al., Int. J. Cancer 41 (1988), 542–547) and the kidney carcinoma cell line A-498 (DSM ACC 55; Giard et al., J. Natl. Cancer Inst. 51 (1973), 1417–1423).

The examination of the number of chromosomes in the genome of a cell line can be performed by using DNA probes which are specific for the particular chromosome and/or the locus of the target gene.

Still another preferred feature of a starting cell line used for an endogenous gene activation is a correct glycosylation of the desired target protein (vii). A human cell line is preferably used which synthesizes the target protein with a glycosylation pattern, especially regarding the number of the sialic acid moieties, comparable to that of the naturally occurring target protein. The test for the presence of a correct glycosylation is performed preferably by transiently transfecting the cell being tested with an extrachromosomal vector which contains the desired target gene under the control of a promoter active in the cell. After transient expression of the target gene the cell supernatant and/or the cell extract is analyzed by isoelectric focusing. With EPO for example, the presence of correct glycosylation is very evident. In the case of in vitro experiments, non-glycosylated EPO, recombinant EPO from E. coli cells for example, has an activity comparable to that of glycosylated EPO. But in in-vivo experiments non-glycosylated EPO is considerably less active. To determine whether a starting cell line is capable of the production of EPO with correct glycosylation, a comparison can be made with urinary EPO, but also with recombinant EPO from CHO cells, which is known to have an active glycosylated form in humans, and its glycosylation is largely identical with urinary EPO. The comparison of the glycosylation is performed preferably by isoelectric focusing.

Still another preferred feature for the selection of a human cell line is the freedom of the tested cell line from infectious contamination (vii), e.g., from infectious viral particles or mycoplasmas. The test for the presence of viral contamination can be performed by means of cell culture, in vivo analyses and/or detection of specific viral proteins.

The invention moreover relates to a method for preparing human proteins by endogenous gene activation in a human cell line, which is characterized in that a cell line is used which has the features (i), (ii), and (iii) specified above, and preferably at least one of the features (iv), (v), (vi), and (vii), as described above, in addition.

The method of the invention is used especially for the production of human factors, such as EPO, thrombopoietin (TPO), colony stimulating factors, such as G-CSF or GM-CSF, proteins which influence blood coagulation, such as tPA, interferons such as IFN-α, IFN-β or IFN-γ, interleukins such as IL-1 to IL-18, chemokines such as MIP, neurotrophic factors such as NGF or BDNF, proteins which affect bone growth such as IFG-BPs, Hedgehog (IgeI) proteins, tumor growth factors such as TFG-β, growth hormones such as HGH, ACTH, encephalins, endorphins, receptors such as, e.g., interleukin or insulin receptors in soluble and/or membrane-standing forms and other protein-binding proteins. With special preference the process for the preparation of EPO is used.

The endogenous gene activation itself can be performed by known methods, and preferably involves the following steps:

(a) Preparation of human starting cell lines which contain at least one copy of an endogenous target gene with the desired nucleic acid sequence, and which, by examining the selection criteria according to the invention, have been identified as suitable for the expression of the target gene, (b) Transfecting the cells with a DNA construct comprising:
  (i) two flanking DNA sequences which are homologous with regions of the target gene locus in order to permit homologous recombination,
  (ii) a positive selection marker gene,
  (iii) a negative selection marker gene if necessary,
  (iv) an amplification gene if desired, and
  (v) a heterologous expression control sequence which is active in the human cell (c) Culturing the transfected cells in conditions which select for the presence of the positive selection marker gene and in some cases the absence of the negative selection marker gene, (d) Analyzing the cells selectable according to step, (e) Identifying the cells producing the desired target protein, and (f) Amplifying the target gene in the selected cells, if desired.

The DNA construct used for making the cell producing the desired human protein contains two flanking DNA sequences homologous to regions of the target gene locus. The choice of suitable flanking sequences is made, for example, according to the methods described in WO90/11354 and WO91/09955. Preferably the flanking sequences have each a length of at least 150 bp.

Especially preferable are the homologous DNA sequences from the 5' region of the target gene, e.g., 5'-untranslated sequences, signal sequence coding exons and introns located in this region, e.g., exon 1 and intron 1.

The positive selection marker gene can be any selection marker gene suitable for eucaryotic cells which upon expression leads to a selectable phenotype, e.g., antibiotic resistance, auxotrophy etc. The neomycin phosphotransferase gene is an especially preferred positive selection marker gene.

Optionally, a negative selection marker gene may be present, such as the HSV thymidine kinase gene by whose expression cells are destroyed in the presence of a selection agent. The negative selection marker gene is located outside of the two flanking homologous sequence regions.

If an amplification of the target gene endogenously activated in the human cell is desired, the DNA construct contains an amplification gene. Examples of suitable amplification genes are a dihydrofolate reductase gene, an adenosine deaminase gene, an ornithine decarboxylase gene, etc. An especially preferred amplification gene is the dihydrofolate reductase gene, especially a gene coding for a dehydrofolate reductase-arginine mutant, which has a higher sensitivity for the selective agent (methotrexate) than the wild type gene (Simonsen et al., Proc. Natl. Acad. Sci., USA 80 (1983), 2495).

Furthermore, the DNA construct used for endogenous gene activation contains a heterologous expression control sequence which is active in a human cell. The expression control sequence comprises a promoter and preferably additional sequences which improve expression, e.g., an enhancer. The promoter can be an inducible or constitutive promoter. Preferably, the promoter is a strong viral promoter, e.g., an SV40 or CMV promoter. The CMV promoter/enhancer is especially preferred.

The invention furthermore relates to the use of the human cell lines identified by the method described above, after the activation of an endogenous target gene present in the cell to obtain the polypeptide encoded by the activated target gene, preferably to obtain the polypeptide in a large-scale technical process, using, for example, a large fermenter.

Still another object of the invention is a human cell which contains a copy of an endogenous gene in operable linkage with a heterologous expression control sequence active in the human cell, and is capable, without prior gene amplification, of the production of at least 200 ng of the polypeptide/$10^6$ cells/24 h. Preferably, the human cell according to the invention is capable of the production of 200 to 3000 ng of polypeptide/$10^6$ cells/24 h, and most preferably capable of the production of 1000 to 3000 ng polypeptide/$10^6$ cells/24 h.

Finally, still another object of the present invention is a human cell which is obtainable by gene amplification from the cell named above and contains several copies of an endogenous gene, each in operable linkage with a heterologous expression control sequence active in the human cell, and is capable of the production of at least 1000 ng of the polypeptide/$10^6$ cells/24 h coded by the endogenous gene. Especially preferred is the human cell line obtainable by gene amplification, capable of the production of 1000 to 25000 ng/polypeptide/$10^6$ cells/24 h. Most preferable is a human cell line capable of the production of 5000 to 25,000 ng polypeptide/$10^6$ cells/24 hr.

An example of a cell according to the invention is the EPO-producing clone, "Aladin," which was deposited on 15 Jul. 1997, according to the provisions of the Budapest Treaty with the Deutsche Sammlung von Mikroorganismen und Zellkulturen (DSMZ), Mascheroder Weg 1b, 38124 Brunswick, under accession number DSM ACC 2320.

The invention is furthermore exemplified by the following examples and figures and a sequence listing.

SEQ ID No. 3 and No. 4 Sequences of the primer used for producing PCR product 2 (FIG. 1).

EXAMPLES

Example 1

Selection Methods 1.1 Determination of the Generation Time

The tested cell lines in a concentration of 0.1–5×$10^5$ per ml, preferably 0.5–2×$10^5$ cells per ml, were seeded in culture dishes with DMEM and 10% FCS and RPMI 1640 and 10% FCS respectively, cultured in a medium recommended by the ATCC, for example, for the particular cells, and under suitable conditions, and the cell count was determined every two to three days with a counting chamber, a Neubauer for example, without and with trypsinization, respectively. Cells which within a week of culturing show 16 to 256 population doublings, preferably 64 to 128 population doublings, were evaluated as positive (+, ++ or +++).

1.2 Culturability in Suspension

To determine culturability in suspension, the cells were cultured for 14 days with constant stirring in a medium (see 1.1 with and without the addition of serum, e.g., fetal calf serum) in a Bellco Spinner with corresponding accessories, at 37° C. and 7% $CO_2$. Cells which during this phase showed at least 5 population doublings were evaluated as suitable (+) for suspension culture.

1.3 Culturability in a Serum-free Medium

To determine culturability in a serum-free medium, the cells were cultured for 14 days at a density of 1–10×$10^5$ cells per ml in culture vessels in the basic medium (i.e., without addition of serum) recommended by ATCC for the particular cells, with ITS (Boehringer Mannheim, Cat. No. 1074547) under the same conditions as in 1.1. Cells which during this period showed at least 5 population doublings (determined by cell count) were evaluated as suitable (+) for the serum-free culture.

1.4 Determination of the Endogenous Expression of the Target Gene

To determine whether the target protein is produced endogenously in the selected cell line, the cells were seeded for 24 hours in a density of 0.01 to 2×$10^6$ cells/ml, preferably 0.5 to 1×$10^6$ cells per milliliter of culture medium. 24 hours later the cell supernatant was removed, the cells discarded, and the content of the cell protein in the supernatant was determined by known methods, e.g., by an immunoassay specific for the particular protein.

In the case of EPO the content was determined by ELISA. For this purpose streptavidin-coated microtitration plates were coated with biotinylated anti-EPO antibodies (Boehringer Mannheim) and incubated with a solution containing protein (1% w/v) to block non-specific binding. Then 0.1 ml of the culture supernatant was added and incubated overnight. After washing, peroxidase-conjugated monoclonal anti-EPO antibodies (Boehringer Mannheim) were added for two hours. The peroxidase reaction was performed using ABTS® as substrate in a Perkin Elmer Photometer at 405 nm.

The EPO detection limit in this test was at 10 pg EPO/ml. Cells which from a seeding of $10^6$ cells/ml produce less than 10 pg EPO/ml were evaluated as nonproducing and as suitable (+).

1.5 Determining the Number of Copies of the Target Gene

To determine the number of copies of the target gene in the cell line, human genomic DNA was isolated from about $10^8$ cells and quantified (Sambrook et al., Molecular Cloning, A Laboratory Manual (1989), Cold Spring harbor Laboratory Press). After cleaving the DNA with restriction enzymes, e.g. AgeI and AscI, and BamHI, HindIII and SalI, respectively, the DNA fragments were separated according to size by agarose gel electrophoresis and lastly transferred to a nylon membrane and immobilized.

The immobilized DNA was hybridized with a DNA probe labeled with digoxigenin, which is specific for the locus of the target gene or the chromosome on which the target gene is situated, and washed under stringent conditions. The specific hybridization signals were detected by a chemoluminescence method using radiation-sensitive films.

1.6 Determining the Nucleic Acid Sequence of the Target Gene

The genomic DNA was isolated from about $10^7$ cells using a DNA isolation kit (e.g., QIAGEN Blood & Cell Culture DNA Kit).

A pair of PCR primers was used for amplification of the target gene. The sequences of the primers were complementary to the sequences which flank the coding region of the target gene. Thus the entire coding region of the target gene could be amplified.

The PCR product was directly sequenced or cloned into a vector and then sequenced. Sequencing primers were used whose sequences are complementary to sequences from the intron regions of the target gene, so that the sequences of the exon regions of the target gene can be preserved completely. The sequencing was performed on a PE/ABI automatic sequencer using, for example, the 'Prism™ Ready Reaction Dye Terminator Cycle Sequencing' Kits (PE/ABI, Forster City, U.S.A.) according to the manufacturer's instructions.

1.7 Determination of the Glycosylation Pattern

To determine the glycosylation pattern of EPO the cell lines to be assayed were transfected with the plasmid pEPO 227 which contains a 4 kb HindIII/EcoRI fragment of the human EPO gene sequence under the control of the SV40 promoter (Jacobs et al. Nature 313 (1985), 806; Lee-Huang et al. Gene 128 (1993), 272). The cells were transfected in the presence of lipofectamine using a commercially available reagent kit according to the manufacturer's instructions. The EPO content in the cell supernatant obtained 2 to 5 days later was determined by ELISA.

The cell supernatant was concentrated and compared with known EPO products by isolectric focusing (Righetti P. G., in: Work T. S., Burdon R. H. (ed.), Isoelectric focusing: Theory, Methodology and Applications, Elsevier Biomedical Press, Amsterdam (1983). Human cells which produced a glycosylation pattern comparable to known EPO products, such as urinary EPO, were rated as suitable (+).

1.8 Detection of Viral Contamination 1.8.1 Analyses by Cell Culture

To detect possible infectious viral contamination of the human cell line being assayed, a lysate of the cells was incubated with a detector cell line to detect cytopathic effects. In addition, hemoadsorption analyses were performed.

To prepare the lysate a suspension of $10^6$ cells in 1 ml of buffer was lysed by a rapid freeze-and-thaw process. The cellular residue was separated by centrifugation and the supernatant was added to the detector cell lines. HepG2 cells (ATCC HB 8065; Nature 282 (1979), 615–616), MRC-5 (ATCC-1587) and Vero (ATCC CCL-171; Jacobs, Nature 227 (1970), 168–170) were used. Viruses of the polio SV and influenza types, were used as positive controls. Detector cell lines, which were cultured without lysate, were used as negative controls. The detector cell lines were regularly tested over a period of at least 14 days to detect cytopathic effects.

For the hemoadsorption analysis, erythrocytes from chickens, pigs or humans were added after 7 days to vero cells which had been incubated with the cell lysates and with the controls. Adhesion of the erythrocytes to the monolayer of the cultured cells indicates viral contamination of the cultures.

1.8.2 In vivo Analysis

Lysates of the cell lines under study were prepared as described in 1.8.1 and injected intraperitoneally or intracerebrally, in an amount of 0.1 ml, into new-born mice. Over a period of 14 days the mice were observed for morbidity and mortality.

1.8.3 Specific Detection of Viral Proteins

The presence of specific viral proteins such as Epstein-Barr virus proteins (nuclear protein or capsid antigen) were tested by adding human serum of EBV-positive bands to immobilized cells of the cell line under test. The detection of the virus antigens was then performed by adding complement and the corresponding anti-human complement C3 fluorescein conjugate (to detect nuclear antigen) or by adding anti-human globulin fluorescein (to detect the capsid antigen).

Example 2

Selection Results

The human cell lines, HepG2, HT1080, Namalwa, HeLa and HeLaS3 were assayed by the methods referred to in Example 1. The results are shown in the following Table 1.

TABLE 1

|  | HepG2 | HT1080 | Namalwa | HeLa | HeLa S3 |
|---|---|---|---|---|---|
| Growth | | | | | |
| Doubling time | + | + + | + + | + + + | + + + |
| Suspension culture | − | + | + | +/− | + |
| Serum-free possible | +/− | + | + | + | + |
| EPO Production | | | | | |
| endogenous transient/ml | + 53 ng | − 65 ng | − 70 ng | − 100 ng | − 480 ng |
| EPO glycosylation (transient) | − | + | + | + | + |
| Test for viral infectious contamination | not tested | free | free | not tested | free |

From Table 1 it is evident that the cell lines HT1080, Namalwa and HeLa S3 are to be considered suitable for the endogenous gene activation of EPO. Namalwa and HeLa S3 are especially suitable.

Example 3

Cloning of EPO Homology Regions

Figure 1:
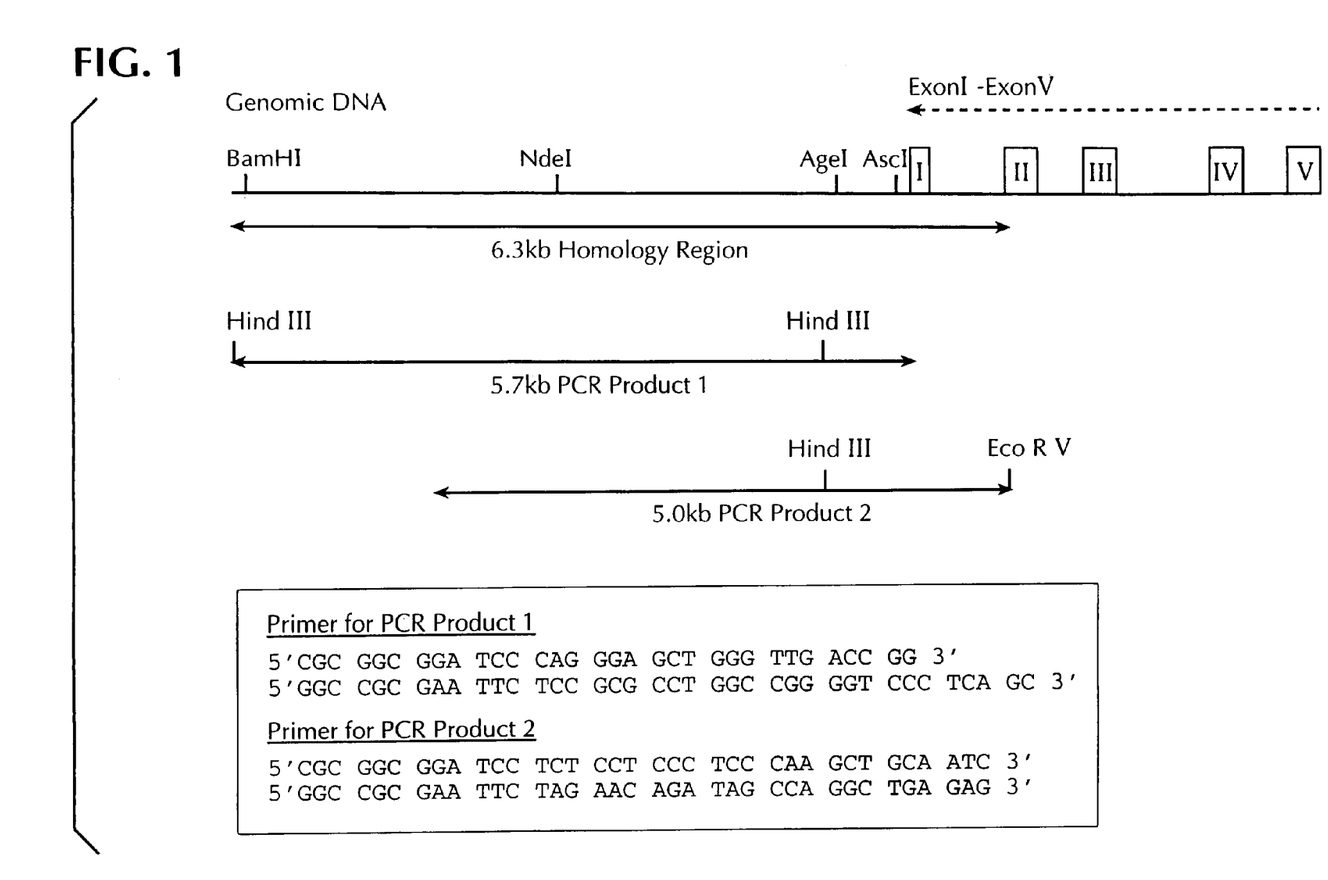
FIG. 1 is a schematic representation of the amplification of homology regions of the EPO gene from the region of the 5'-untranslated sequences, exon 1 and intron 1, FIG. 2 a schematic representation of a plasmid which contains EPO homology regions from the region of the 5'-untranslated sequences, exon 1 and intron 1, FIG. 3 a schematic representation of a gene activation sequence which contains the Rous sarcoma virus promoter (RSV), the neomycin phosphotransferase gene (NEO), the early polyadenylation region of SV40 (SVIpA), the early SV40 promoter (SVI), the dihydrofolate reductase gene (DHFR) and the cytomegalovirus immediate-early promoter and enhancer (MCMV), FIG. 4*a* the preparation of the EPO gene targeting vector p176, FIG. 4*b* the preparation of the EPO gene targeting vectors p179 and p187, FIG. 4*c* the preparation of the EPO gene targeting vector p189, FIG. 4*d* the preparation of the EPO gene targeting vector p190, FIG. 4*e* the preparation of the EPO gene targeting vector p192, SEQ ID No. 1 and No. 2 nucleotide sequences of the primer used for producing PCR product 1 (FIG. 1)

Homology regions of the EPO gene were amplified by PCR using a genomic placental DNA (Boehringer Mannheim). Two PCR products were prepared from a homology region 6.3 kB long from the region of the 5'-untranslated sequences of the EPO gene, exon 1 and intron 1 (cf. FIG. 1). The primers used in preparing the PCR Product 1 had the following sequences: 5'-CGC GGC GGA TCC CAG GGA GCT GGG TTG ACC GG-3' (SEQ ID No. 1) and 5'-GGC CGC GAA TTC TCC GCG CCT GGC CGG GGT CCC TCA GC-3' (SEQ ID No. 2). The primers used in preparing PCR Product 2 had the following sequences: 5'-CGC GGC GGA TCC TCT CCT CCC TCC CAA GCT GCA ATC-3' (SEQ ID No. 3) and 5'-GGC CGC CGC GAA TTC TAG AAC AGA TAG CCA GGC TGA GAG-3' (SEQ ID No. 4).

Figure 2:
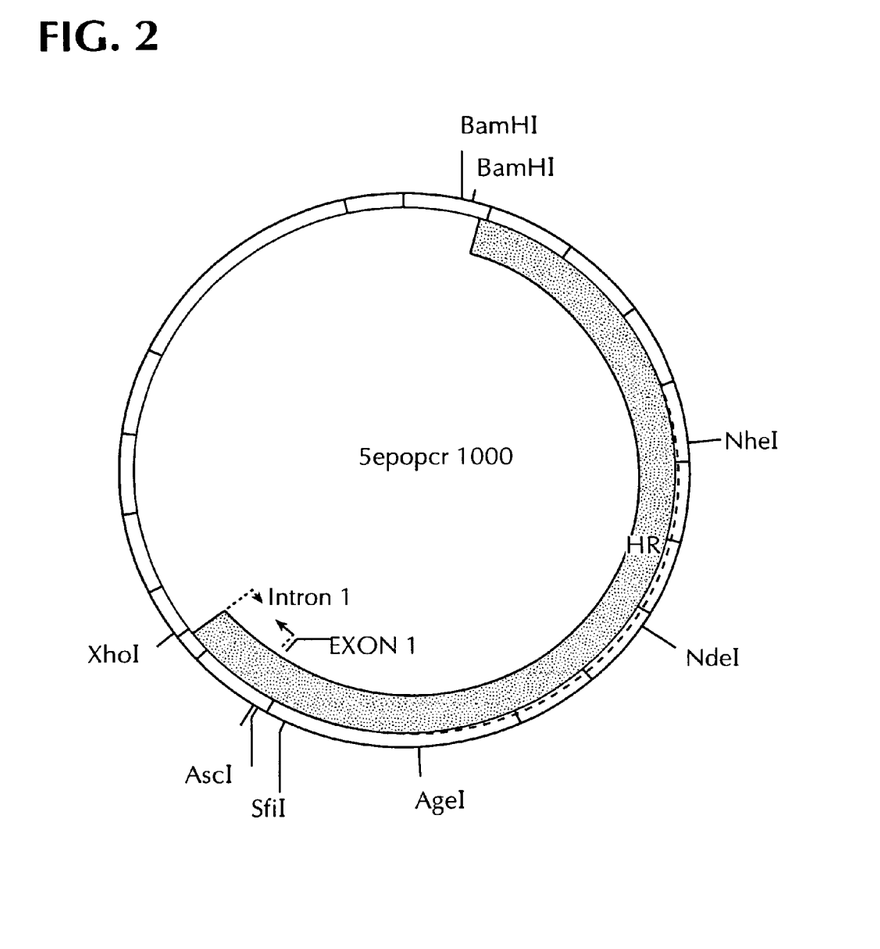

The desired segments were cut out of PCR Products 1 and 2 by restriction cleavage (PCR Product 1; HindIII, PCR Product 2: HindIII and Eco RV) and cloned into the vector pCRII (Invitrogen) which had been cleaved with HindIII and Eco RV. The recombinant vector obtained in this manner was designated a 5epopcr1000 (cf. FIG. 2).

Example 4

Figure 3:
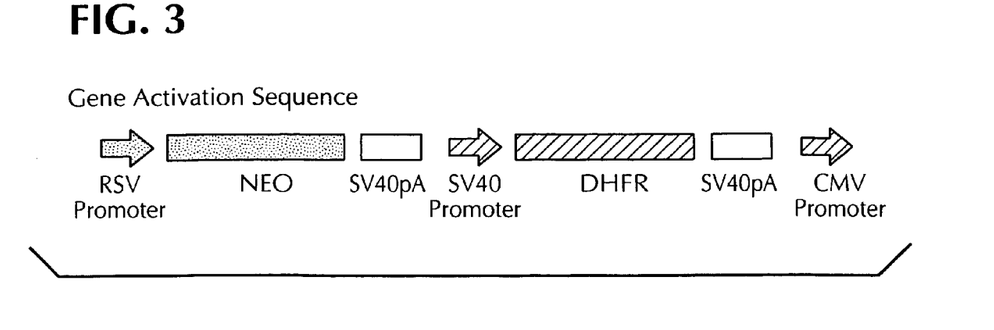
Figure 4A:
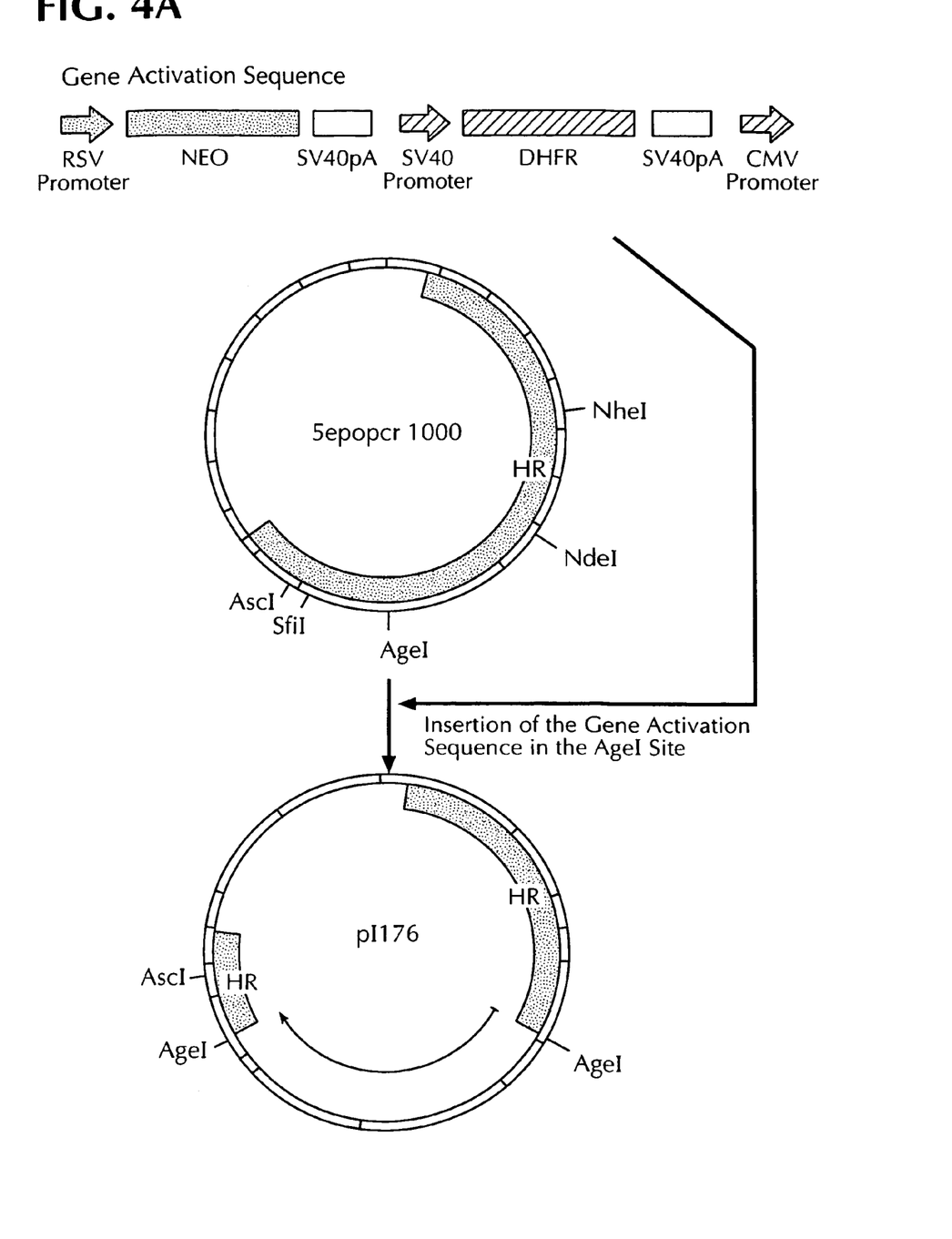
Figure 4B:
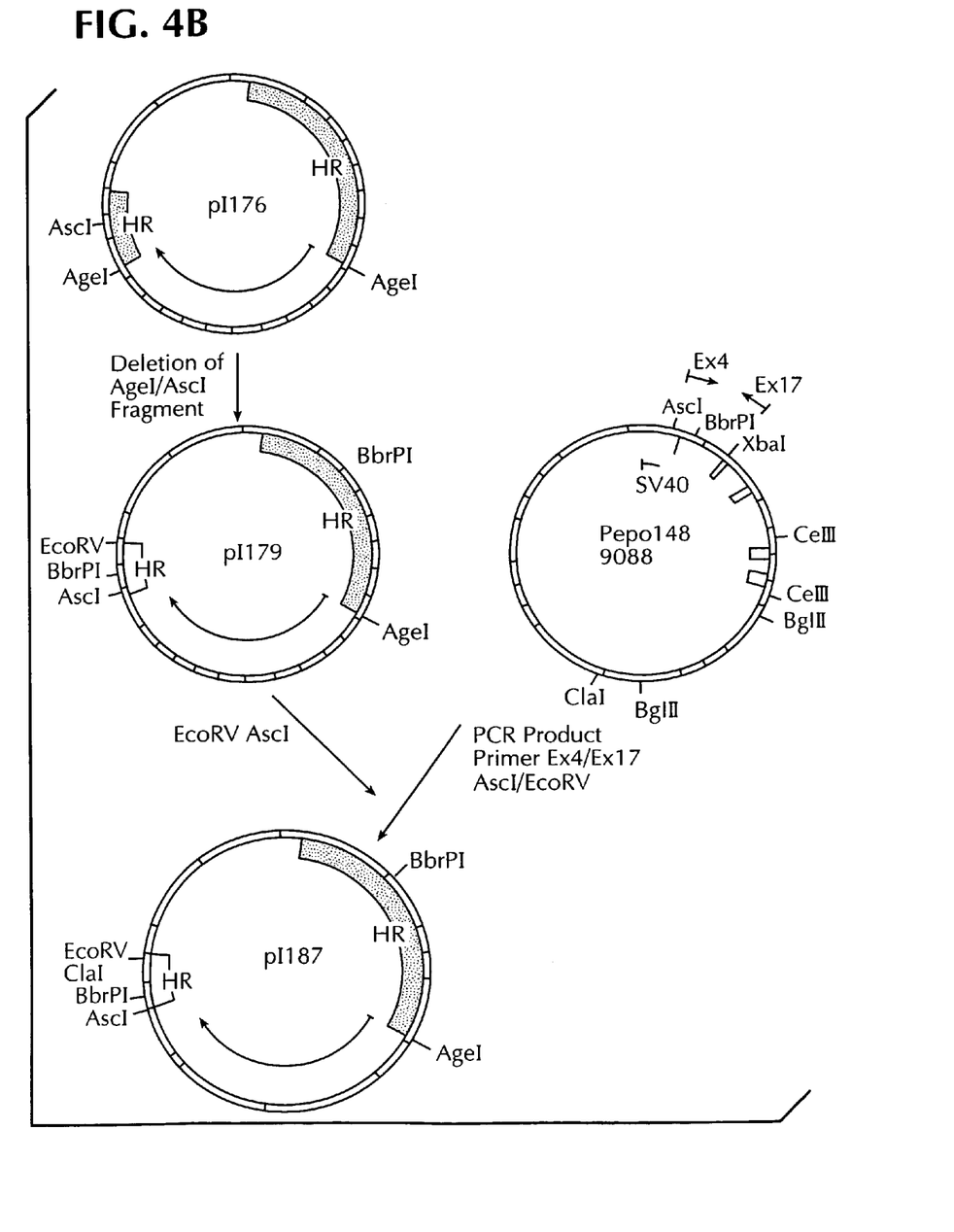
Figure 4C:
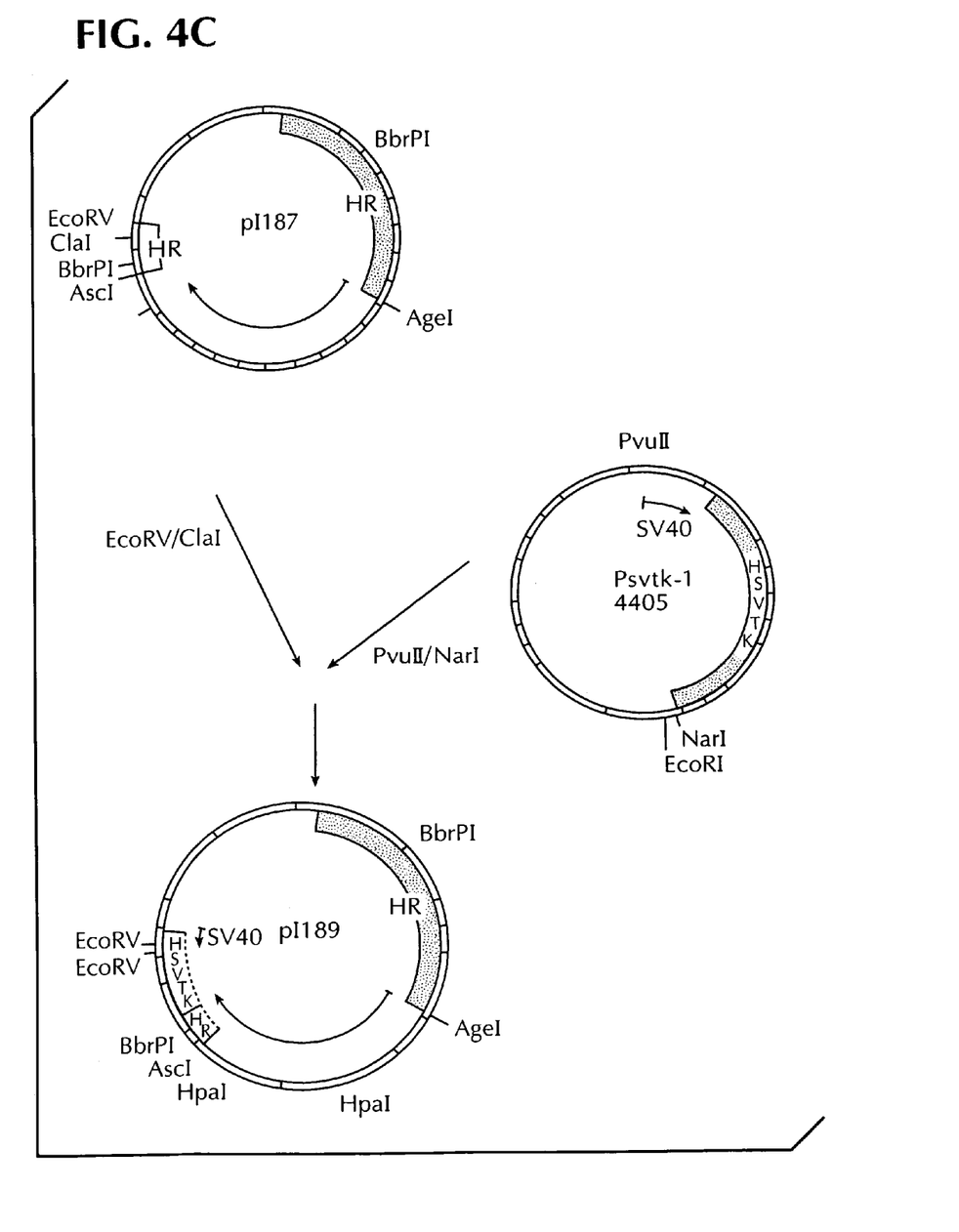
Figure 4D:
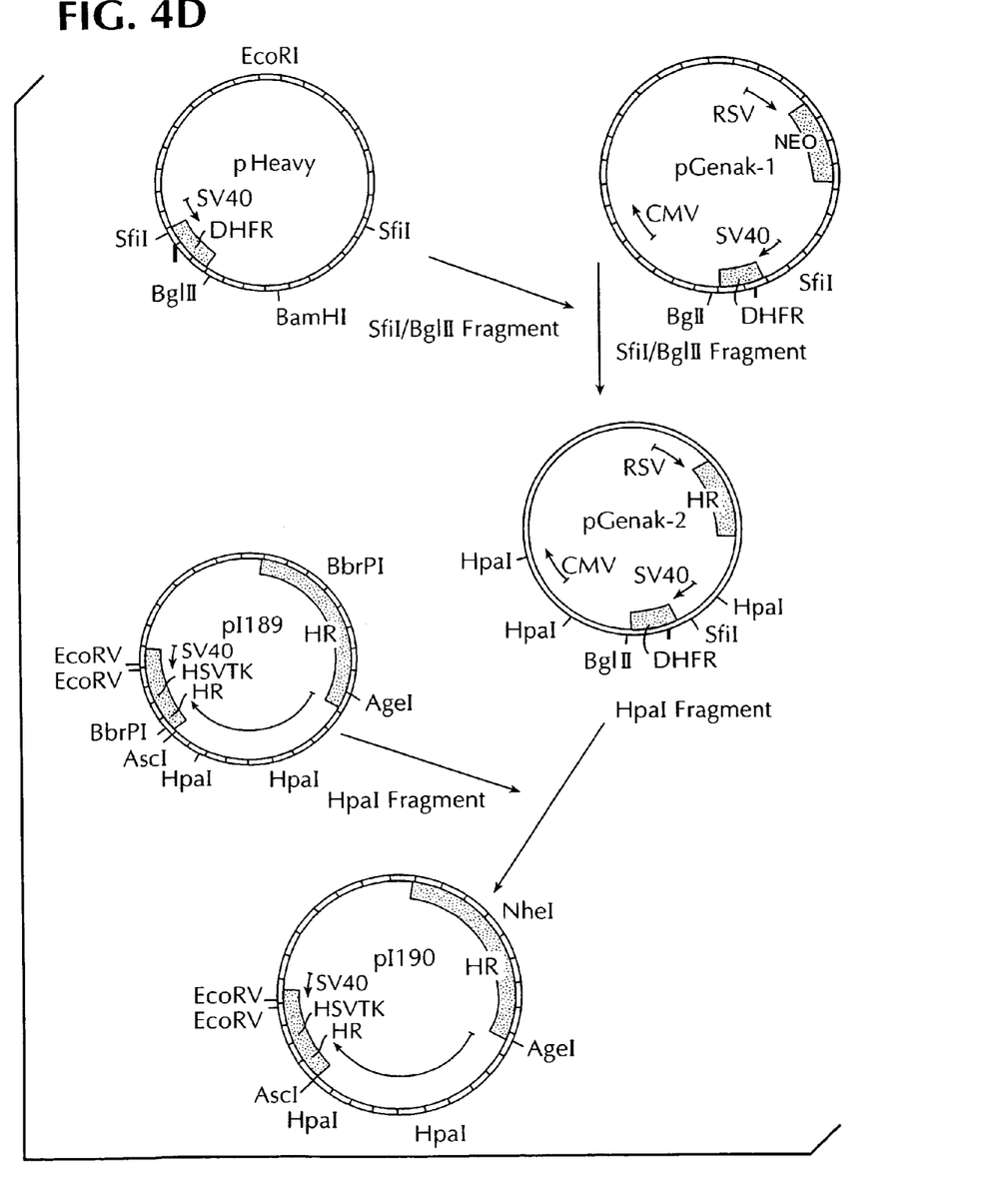
Figure 4E:
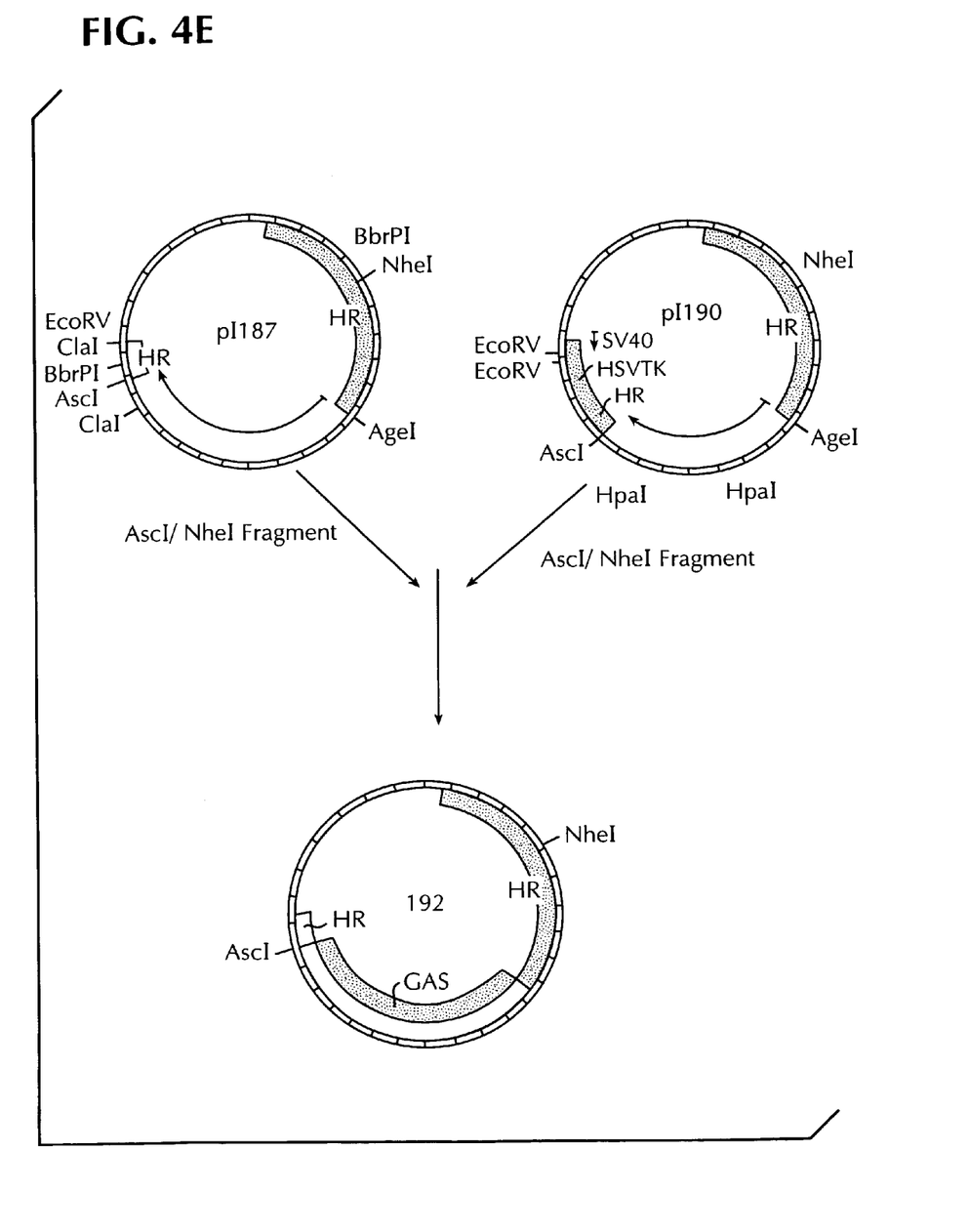

Construction of EPO Gene Targeting Vectors 4.1 A gene activation sequence which contains the NEO gene, the DHFR gene and a CMV promoter/enhancer (cf. FIG. 3) was inserted into the AgeI site of the plasmid Sepocr1000 containing the EPO homology region, to produce plasmid p176 (cf FIG. 4a). To bring the CMV promoter as close as possible to the translation initiation site a segment 963 bp long between the restriction sites AscI and AgeI was deleted (partial cleavage), to produce plasmid p179 (FIG. 4b).
4.2 To optimize the expression, nucleotides in exon 1, which code for the start of the EPO leader sequence Met-Gly-Val-His, were replaced with the synthetic sequence Met-Ser-Ala-His. This sequence was obtained by amplification of a genomic EPO DNA sequence, e.g., of the plasmid pEPO148, which contains a 3.5 kB BstEII/EcoRI fragment (including the exons 1–5) of the human EPO gene sequence under the control of the SV40 promoter (Jacobs et al., Nature 313 (1985),806, and Lee-Huang et al., Gene 128 (1993), 227), as template with corresponding primers. Thus the plasmid p187 was obtained (FIG. 4b).
4.3 The plasmid p189 was prepared from the plasmid p187 by insertion of the Herpes Simplex Virus-thymidine kinase gene (HSV-TK) which originated from Psvtk-1 (PvuII/NarI fragment) (FIG. 4c). The HSV-TK gene is under the control of the SV40 promoter at the 3' end of intron I (EcoRV/ClaI) in opposite orientation relative to the CMV promoter and should serve for negative selection for homologous recombination.
4.4 For the construction of plasmid p190 an SfiI/BglII fragment of pHEAVY, a plasmid which contains the cDNA of an arginine mutant of DHFR described in Simonsen et al. (Proc. Natl. Acad. Sci. USA 80 (1983), 2495), was subcloned into the plasmid pGenak-1 digested with SfiI and BglII, which contains the NEO gene under control of the RSV promoter and the late SV40 polyadenylation site as terminator, the murine DHFR gene under control of the early SV40 promoter and the early SV40 polyadenylation site as terminator (Kauffmann et al., Mol. Cell. Biol. 2 (1982), 1304; Okayama et al., Mol. Cell. Biol. 3 (1983), 280 and Schinke, J. Biol. Chem. 263 (1988), 5989) and the CMV promoter (Boshart et al., Cell 41 (1995), 521). Then an HpaI fragment which contains the cDNA coding for the DHFR-argenine mutant was ligated into the plasmid p189 cleaved with HpaI, whereupon the plasmid p190 was obtained (FIG. 4d).
4.5 To obtain a transfection vector without the HSV-TK gene, an AscI/NheI fragment of the plasmid p190 which contains the gene activation sequence, was ligated into the AscI/NheI fragment of the plasmid p187 containing exon 1. The resulting plasmid was named p192 (FIG. 4e).

Example 5

Transfection of Cells

Various cell lines were selected for the production of EPO and transfected with targeting vectors.

5.1 Namalwa Cells

The cells were cultured in T150 tissue culture bottles and transfected by electroporation ($1 \times 10^7$ cells/800 µl electroporation buffer 20 mM Hepes, 138 mM NaCl, 5 mM KCl, 0.7 mM $Na_2HPO_4$, 6 mM D-glucose monohydrate pH 7.0, 10 µg linearized DNA, 960 µF, 260 V BioRad Gene Pulser). After electroporation the cells were cultured in RPMI 1640, 10% (v/v) fetal calf serum (FCS), 2 mM L-glutamine, 1 mM sodium pyruvate in forty 96-well plates. After two days the cells were cultured for 10 to 20 days in medium containing 1 mg/ml G-418. The supernatant was assayed in a solid-phase ELISA for the production of EPO (see Example 1.4). The EPO-producing clones were expanded in 24-well plates and T-25 tissue culture bottles. Aliquots were frozen and the cells were subcloned by FACS (Ventage, Becton Dickinson). The subclones were repeatedly tested for EPO production.

5.2 HT 1080 Cells

The conditions were as described for Namalwa cells, except that the HT 1080 cells were cultured in DMEM, 10% (v/v) FCS, 2 mM L-glutamine, 1 mM sodium pyruvate. For transfection by electroporation the cells were released from the walls of the culture vessels by trypsinization. After electroporation, $1 \times 10^7$ cells were cultured in DMEM, 10% (v/v) FCS, 2 mM L-glutamine and 1 mM sodium pyruvate in five 96-well plates.

5.3 HeLa S3 Cells

The conditions were as described for Namalwa cells, except that the HeLaS3 cells were cultured in RPMI 1640, 10% (v/v) FCS, 2 mM L-glutamine, 1% (v/v) NEM nonessential amino acids (Sigma), and 1 mM sodium pyruvate. For transfection by electroporation, the cells were released from the walls of the culture vessels by trypsinization. The conditions for the electroporation were 960 µF/250 V. After the electroporation the cells were cultured in RPMI 1640, 10% (v/v) FCS,2 mM L-glutamine, 1% (v/v) NEM, 1 mM sodium pyruvate in T75 tissue culture flasks. 24 hours after electroporation the cells were trypsinized and cultured for 10 to 15 days in a medium containing 600 µg/ml G-418 in ten 96-well plates.

Example 6

EPO Gene Amplification

To increase the EPO expression, the EPO-producing clones were cultured in the presence of increasing concentrations (100 pM–1000 nM) of methotrexate (MTX). In each MTX concentration the clones were tested by an ELISA (see example 1.4) for the production of EPO. Strong producers were subcloned by limiting dilution.

Example 7

Characterization of EPO-Producing Cell Lines

Three different cell lines (Namalwa, HeLa S3 and HT 1080) were selected for EPO gene activation. EPO-producing clones were obtained by transfection with the plasmids p179, p187, p189, p190 or p192 (cf. Examples 2 and 3).

Approximately 160,000 NEO-resistant clones were tested for EPO production, of which 12 to 15 secreted EPO in the cell supernatant, repeatably in significant yield.

Of these a total of 7 EPO clones were identified surprisingly without gene amplification with MTX, and produced EPO in sufficient amounts for a large industrial production. The EPO production of these clones ranged from 200 ng/ml to more than 1000 ng/ml/$10^6$ cells/24 h.

After gene amplification with 500 nM MTX the EPO production of the identified EPO clones was increased to more than 3000 ng/ml/$10^6$ cells/24 h. A further increase in the MTX concentration up to 1000 nM resulted in a production of up to more than 7000 ng/ml/$10^6$ cells/24 h.

The clones obtained showed an EPO production also under serum-free culture conditions and in the absence of MTX.

---

The invention claimed is:

1. A human cell line characterized in that it contains a copy of an endogenous gene in operable linkage with a CMV or SV40 promoter active in the human cell and is capable of the production of at least 200 ng of the polypeptide encoded by the endogenous gene/$10^6$ cells/24 h, wherein said endogenous gene is an erythropoietin (EPO) gene.

2. A human cell line characterized in that it contains at least two copies of an endogenous gene, each in operative connection with a CMV or SV40 promoter active in the human cell, and is capable of the production of at least 1000 ng of the polypeptide encoded by the endogenous gene/$10^6$ cells/24 h, wherein said endogenous gene is an erythropoietin (EPO) gene.

3. A method for obtaining a polypeptide encoded by a target gene endogenously present in a cell comprising
    (a) assaying a human cell line for the presence of the following features:
        (i) a target gene with the desired nucleic acid sequence,
        (ii) at least 5 population doublings within 14 days in a suspension culture, and
        (iii) at least 5 population doublings within 14 days in a serum-free culture medium,
    (b) selecting a cell line satisfying features (i), (ii) and (iii),
    (c) activating the target gene endogenously present in the cell by endogenous activation of the target gene,
    (d) culturing the cell of (c) under conditions suitable for production of the polypeptide of the activated target gene, and
    (e) obtaining the polypeptide from the cells of (d).

4. Method according to claim 3, characterized in that the human cell line has (iv) a generation time of 16 to 256 population doublings within one week in a culture medium.

5. Method according to claim 4, characterized in that the human cell line has 64 to 128 population doublings within one week in a culture medium.

6. Method according to claim 3, characterized in that the human cell line (v) shows no substantial endogenous expression of the target gene.

7. Method according to claim 3, characterized in that the human cell line (vi) contains more than 2 chromosomal copies of the target gene.

8. The method according to claim 3, characterized in that the human cell line (vii) synthesizes the polypeptide with a glycosylation pattern comparable to the naturally occurring target protein.

9. The method according to claim 3, characterized in that the human cell line is (viii) free of detectable infectious contamination.

10. The method of claim 3, characterized in that the cell line furthermore satisfies at least one of features
    (iv) a generation time of 16 to 256 population doublings within one week in a culture medium,
    (v) shows no substantial endogenous expression of the target gene,
    (vi) contains more than 2 chromosomal copies of the target gene,
    (vii) synthesizes the polypeptide with a glycosylation pattern comparable to the naturally occurring target protein or
    (viii) free of detectable infectious contamination.

11. Method according to claim 3 wherein said polypeptide is a human factor selected from EPO, TPO, colony stimulating factors, proteins which affect blood coagulation, interferons, interleukins, chemokines, neurotrophic factors, proteins which affect bone growth, hedgehog proteins, tumor growth factor, growth hormones, ACTH, encephalins, endorphins, receptors and other protein-binding proteins.

12. Method according to claim 11 wherein the human factor is EPO.

13. The method of claim 3 wherein the cells of (c) are cultured in a fermenter.

* * * * *